(12) United States Patent
Spitler et al.

(10) Patent No.: US 7,588,588 B2
(45) Date of Patent: Sep. 15, 2009

(54) SYSTEM AND METHOD FOR STABILIZING OF INTERNAL STRUCTURES

(75) Inventors: James Spitler, Frisco, TX (US); Scott Schorer, Longmont, CO (US)

(73) Assignee: Innovative Spinal Technologies, Plano, TX (US)

(*) Notice: Subject to any disclaimer, the term of this patent is extended or adjusted under 35 U.S.C. 154(b) by 343 days.

(21) Appl. No.: 10/690,211

(22) Filed: Oct. 21, 2003

(65) Prior Publication Data

US 2005/0085813 A1    Apr. 21, 2005

(51) Int. Cl.
*A61B 17/70* (2006.01)
(52) U.S. Cl. ............... 606/246; 606/279; 606/86 A; 606/914; 606/256; 606/104
(58) Field of Classification Search .......... 606/61, 606/72–73, 246–279, 300–331, 86 A, 104, 606/914, 916
See application file for complete search history.

(56) References Cited

U.S. PATENT DOCUMENTS

| | | |
|---|---|---|
| 1,522,927 A | 1/1925 | Wickstrom et al. |
| 1,712,196 A | 5/1929 | Burger et al. |
| 2,058,942 A | 3/1936 | Bailey |
| 2,248,054 A | 7/1941 | Becker |
| 2,302,691 A | 11/1942 | Green |
| 2,329,398 A | 9/1943 | Duffy |
| 2,952,285 A | 9/1960 | Roosli |
| 3,989,284 A | 11/1976 | Blose |
| 4,140,111 A | 2/1979 | Morrill |
| 4,361,141 A | 11/1982 | Tanner |
| 4,433,677 A | 2/1984 | Ulrich |
| 4,719,905 A | 1/1988 | Steffee |
| 4,771,767 A | 9/1988 | Steffee |
| 4,827,918 A | 5/1989 | Olerud |
| 4,917,409 A | 4/1990 | Reeves |
| 4,950,269 A | 8/1990 | Gaines, Jr. |
| 5,042,982 A | 8/1991 | Harms |
| 5,047,029 A | 9/1991 | Aebi et al. |
| 5,102,412 A | 4/1992 | Rogozinski |

(Continued)

FOREIGN PATENT DOCUMENTS

DE    8910080    12/1989

(Continued)

OTHER PUBLICATIONS

International Search Report issued for PCT/US2004/035000, dated Mar. 2, 2005.

(Continued)

*Primary Examiner*—Eduardo C Robert
*Assistant Examiner*—Mary Hoffman
(74) *Attorney, Agent, or Firm*—Eckert Seamans Cherin & Mellott, LLC

(57) ABSTRACT

There is shown a system and method for reducing the difficulty in percutaneous placement of a spine stabilization brace. A medical implant system has a first bone anchor having a longitudinal axis, a second bone anchor and a brace. The brace couples the first bone anchor to the second bone anchor. A the distal end of the brace may be pivotally coupled to the first bone anchor and also adapted to slide in a generally transverse direction in relation to the longitudinal axis of the first bone anchor.

6 Claims, 14 Drawing Sheets

U.S. PATENT DOCUMENTS

| | | |
|---|---|---|
| 5,116,337 A | 5/1992 | Johnson |
| 5,120,171 A | 6/1992 | Lasner |
| 5,171,279 A | 12/1992 | Mathews |
| 5,176,680 A * | 1/1993 | Vignaud et al. ............... 606/61 |
| 5,196,014 A * | 3/1993 | Lin .............................. 606/61 |
| 5,196,015 A | 3/1993 | Neubardt |
| 5,207,678 A | 5/1993 | Harms |
| 5,258,016 A | 11/1993 | Dipoto et al. |
| 5,261,913 A | 11/1993 | Marnay |
| 5,312,438 A | 5/1994 | Johnson |
| 5,330,472 A | 7/1994 | Metz-Stavenhagen |
| 5,360,431 A | 11/1994 | Puno et al. |
| 5,375,823 A | 12/1994 | Navas |
| 5,387,212 A | 2/1995 | Yuan et al. |
| 5,387,213 A | 2/1995 | Breard |
| 5,409,488 A | 4/1995 | Ulrich |
| 5,425,732 A | 6/1995 | Ulrich |
| 5,458,608 A | 10/1995 | Wortrich |
| 5,466,237 A | 11/1995 | Byrd, III et al. |
| 5,468,241 A | 11/1995 | Metz-Stavenhagen |
| 5,474,555 A | 12/1995 | Puno et al. |
| 5,480,440 A | 1/1996 | Kambin |
| 5,486,174 A | 1/1996 | Fournet-Fayard |
| 5,496,321 A | 3/1996 | Puno |
| 5,520,689 A * | 5/1996 | Schlapfer et al. ............... 606/61 |
| 5,526,812 A | 6/1996 | Dumoulin et al. |
| 5,536,268 A * | 7/1996 | Griss ........................... 606/61 |
| 5,540,688 A | 7/1996 | Navas |
| 5,569,246 A | 10/1996 | Ojima |
| 5,571,102 A | 11/1996 | Cavagna |
| 5,605,457 A | 2/1997 | Bailey et al. |
| 5,605,458 A | 2/1997 | Bailey et al. |
| 5,607,304 A | 3/1997 | Bailey et al. |
| 5,607,425 A | 3/1997 | Rogozinski |
| 5,628,740 A | 5/1997 | Mullane |
| 5,643,260 A | 7/1997 | Doherty |
| 5,667,513 A | 9/1997 | Torrie et al. |
| 5,672,176 A | 9/1997 | Biedermann et al. |
| 5,704,936 A | 1/1998 | Mazel |
| 5,716,355 A * | 2/1998 | Jackson et al. ................ 606/61 |
| 5,716,357 A | 2/1998 | Rogozinski |
| 5,725,581 A | 3/1998 | Branemark |
| 5,733,286 A | 3/1998 | Errico et al. |
| 5,741,268 A | 4/1998 | Schutz |
| 5,876,403 A * | 3/1999 | Shitoto ........................ 606/61 |
| 5,904,682 A | 5/1999 | Rogozinski |
| 5,910,142 A | 6/1999 | Tatar |
| 5,961,516 A | 10/1999 | Graf |
| 5,984,923 A * | 11/1999 | Breard ........................ 606/61 |
| 6,010,504 A | 1/2000 | Rogozinski |
| 6,017,343 A | 1/2000 | Rogozinski |
| 6,074,391 A | 6/2000 | Metz-Stavenhagen et al. |
| 6,077,262 A * | 6/2000 | Schlapfer et al. ............... 606/61 |
| 6,090,113 A | 7/2000 | Le Couedic et al. |
| 6,113,604 A * | 9/2000 | Whittaker et al. .............. 606/72 |
| 6,132,433 A | 10/2000 | Whelan |
| 6,235,028 B1* | 5/2001 | Brumfield et al. .............. 606/53 |
| 6,248,105 B1 | 6/2001 | Schläpfer et al. |
| 6,254,146 B1 | 7/2001 | Church |
| 6,264,658 B1* | 7/2001 | Lee et al. ...................... 606/61 |
| 6,273,914 B1 | 8/2001 | Papas |
| 6,296,642 B1 | 10/2001 | Morrison et al. |
| 6,296,644 B1 | 10/2001 | Saurat |
| 6,302,888 B1 | 10/2001 | Mellinger et al. |
| 6,340,363 B1 | 1/2002 | Bolger et al. |
| 6,342,056 B1* | 1/2002 | Mac-Thiong et al. ......... 606/96 |
| RE37,665 E | 4/2002 | Ralph et al. |
| 6,368,321 B1 | 4/2002 | Jackson |
| 6,371,957 B1 | 4/2002 | Amerin et al. |
| 6,402,757 B1 | 6/2002 | Moore et al. |
| 6,482,207 B1 | 11/2002 | Errico |
| 6,485,491 B1 | 11/2002 | Farris et al. |
| 6,488,682 B2 | 12/2002 | Kikuchi |
| 6,530,929 B1 | 3/2003 | Justis et al. |
| 6,546,277 B1 | 4/2003 | Franck et al. |
| 6,551,316 B1 | 4/2003 | Rinner et al. |
| 6,551,318 B1* | 4/2003 | Stahurski ...................... 606/61 |
| 6,626,904 B1* | 9/2003 | Jammet et al. ................. 606/61 |
| 6,660,006 B2 | 12/2003 | Markworth et al. |
| 6,726,689 B2 | 4/2004 | Jackson |
| 6,726,692 B2 | 4/2004 | Bette |
| 6,749,613 B1 | 6/2004 | Conchy |
| 6,755,829 B1 | 6/2004 | Bono et al. |
| 6,770,075 B2* | 8/2004 | Howland ...................... 606/61 |
| 6,786,907 B2 | 9/2004 | Lange |
| 6,802,844 B2 | 10/2004 | Ferree |
| 6,827,722 B1 | 12/2004 | Schoenefeld |
| 6,837,889 B2 | 1/2005 | Shluzas |
| 6,932,822 B2 | 8/2005 | Oribe |
| 6,979,334 B2 | 12/2005 | Dalton |
| 7,083,621 B2* | 8/2006 | Shaolian et al. ............... 606/61 |
| 2001/0034526 A1 | 10/2001 | Kuslich et al. |
| 2002/0095153 A1 | 7/2002 | Jones et al. |
| 2002/0123754 A1 | 9/2002 | Holmes et al. |
| 2002/0138077 A1 | 9/2002 | Ferree |
| 2003/0105460 A1* | 6/2003 | Crandall et al. ............... 606/61 |
| 2003/0153911 A1 | 8/2003 | Shluzas |
| 2003/0199872 A1 | 10/2003 | Markworth |
| 2003/0208203 A1* | 11/2003 | Lim et al. ..................... 606/61 |
| 2004/0039384 A1* | 2/2004 | Boehm, Jr. et al. ............ 606/61 |
| 2004/0049191 A1 | 3/2004 | Markworth |
| 2004/0049196 A1 | 3/2004 | Jackson |
| 2004/0133203 A1* | 7/2004 | Young et al. .................. 606/61 |
| 2004/0138662 A1* | 7/2004 | Landry et al. ................. 606/61 |
| 2004/0143265 A1 | 7/2004 | Landry et al. |
| 2004/0147936 A1 | 7/2004 | Rosenberg et al. |
| 2004/0172022 A1 | 9/2004 | Landry et al. |
| 2004/0176766 A1 | 9/2004 | Shluzas |
| 2004/0215190 A1 | 10/2004 | Nguyen |
| 2004/0254576 A1 | 12/2004 | Dunbar |
| 2004/0260287 A1 | 12/2004 | Ferree |
| 2004/0267275 A1 | 12/2004 | Cournoyer et al. |
| 2004/0276275 | 12/2004 | Coumoyer |
| 2005/0033299 A1 | 2/2005 | Shluzas |
| 2005/0065517 A1 | 3/2005 | Chin et al. |
| 2005/0070917 A1 | 3/2005 | Justis |
| 2005/0070918 A1 | 3/2005 | Zwirnmann et al. |
| 2005/0080418 A1 | 4/2005 | Simonson |
| 2005/0085813 A1 | 4/2005 | Spitler et al. |
| 2005/0090824 A1 | 4/2005 | Shluzas |
| 2005/0107788 A1 | 5/2005 | Beaurain |
| 2005/0131408 A1 | 6/2005 | Sicvol et al. |
| 2005/0131419 A1 | 6/2005 | McCord |
| 2005/0131420 A1 | 6/2005 | Techiera |
| 2005/0131421 A1 | 6/2005 | Anderson |
| 2005/0131422 A1 | 6/2005 | Anderson |
| 2005/0137593 A1 | 6/2005 | Gray |
| 2005/0149023 A1 | 7/2005 | Ritland |
| 2005/0149036 A1 | 7/2005 | Varieur |
| 2005/0149053 A1 | 7/2005 | Varieur |
| 2005/0154389 A1 | 7/2005 | Selover |
| 2005/0171540 A1 | 8/2005 | Lim |
| 2005/0171549 A1 | 8/2005 | Boehm, Jr. |
| 2005/0277919 A1 | 12/2005 | Slivka |
| 2005/0283244 A1 | 12/2005 | Gordon |
| 2006/0149252 A1 | 7/2006 | Markworth et al. |

FOREIGN PATENT DOCUMENTS

| | | |
|---|---|---|
| DE | 9402695 | 5/1994 |
| DE | 9402695 U1 | 5/1994 |
| DE | 29903342 U1 | 7/1999 |
| DE | 29810798 U1 | 12/1999 |
| EP | 159007 A3 | 4/1986 |

| | | | | | | | | | |
|---|---|---|---|---|---|---|---|---|---|
| EP | 107228 | * | 1/2001 | ................ 606/61 | WO | WO2004047650 | A3 | 6/2004 | |
| EP | 1072228 | A1 | 1/2001 | | WO | WO2004082464 | A3 | 9/2004 | |
| EP | 1281365 | A1 | 2/2003 | | WO | WO2005041799 | A1 | 5/2005 | |
| EP | 1190678 | A3 | 3/2003 | | WO | WO03/026523 | | 11/2005 | |
| FR | 2659546 | A1 | 9/1991 | | WO | WO2005/110257 | A1 | 11/2005 | |
| FR | 2698533 | | 6/1994 | | WO | WO2005/117731 | A1 | 12/2005 | |
| FR | 2697428 | | 9/1997 | | WO | WO2005/122926 | A1 | 12/2005 | |
| FR | 2775583 | | 8/2000 | | WO | WO2005/122930 | A2 | 12/2005 | |
| FR | 2795622 | | 9/2001 | | | | | | |
| GR | 1003754 | | 1/2002 | | | | | | |
| WO | WO98/48717 | | 11/1998 | | | | | | |
| WO | WO0128436 | A1 | 4/2001 | | | | | | |
| WO | WO02/24087 | A1 | 3/2002 | | | | | | |
| WO | WO2005/104970 | | 4/2003 | | | | | | |
| WO | WO03094741 | A2 | 11/2003 | | | | | | |
| WO | WO 2004/017847 | A2 | 3/2004 | | | | | | |
| WO | WO 2004/041100 | A1 | 5/2004 | | | | | | |

OTHER PUBLICATIONS

Partial International Search Report issued for PCT/US2005/036339 dated Jan. 23, 2006.

Hoffman, Mary C.; USPTO Office Action in U.S. Appl. No. 10/990,272 dated Apr. 8, 2008.

* cited by examiner

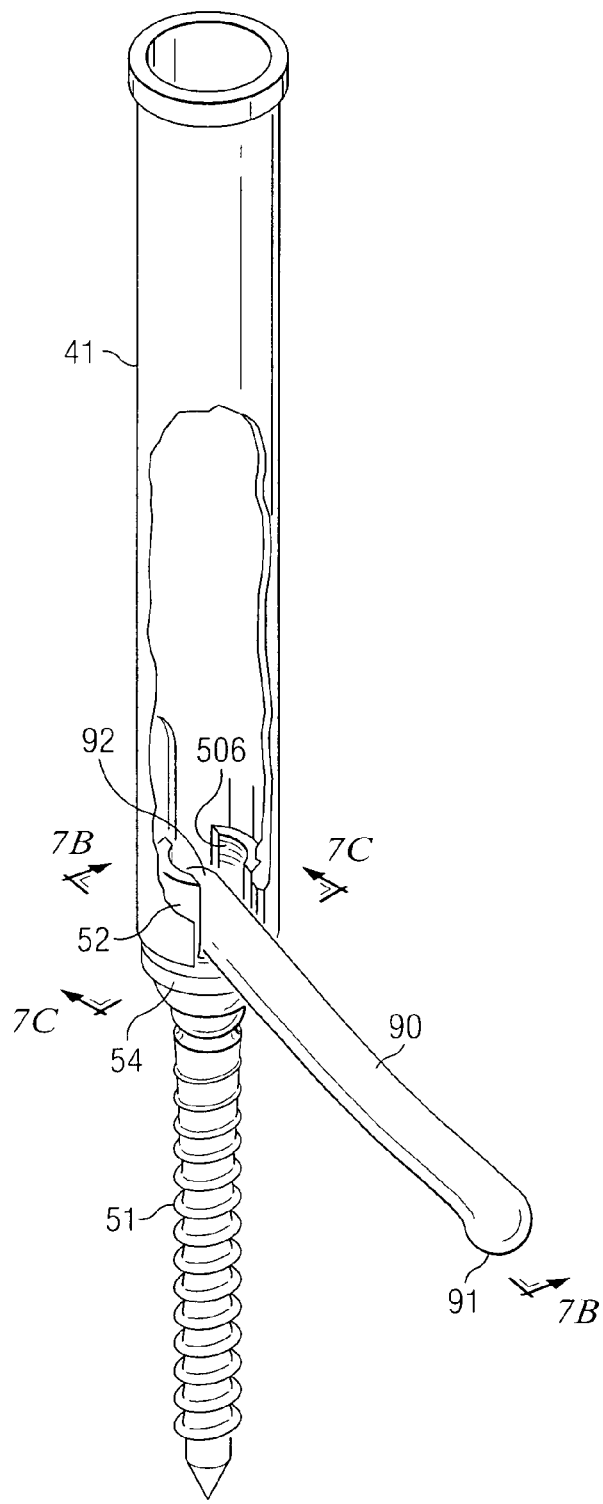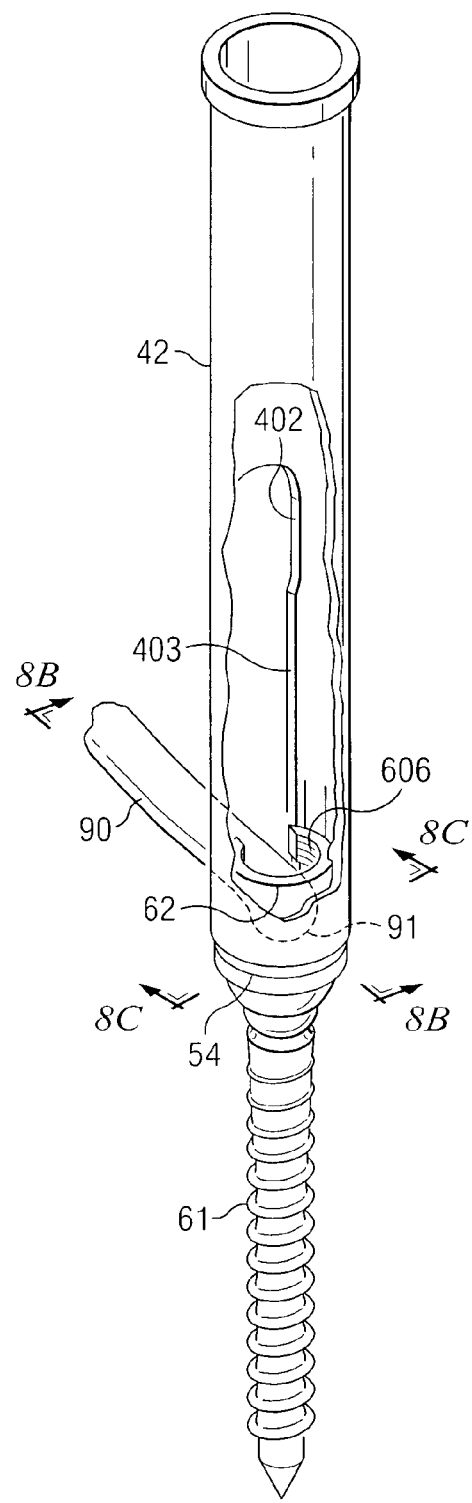

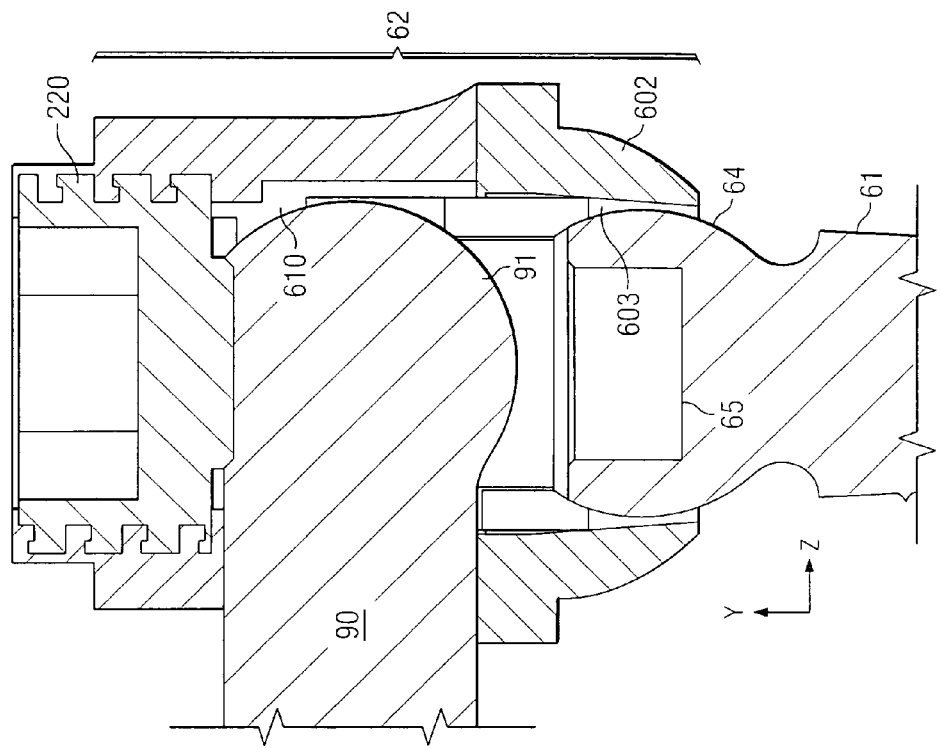
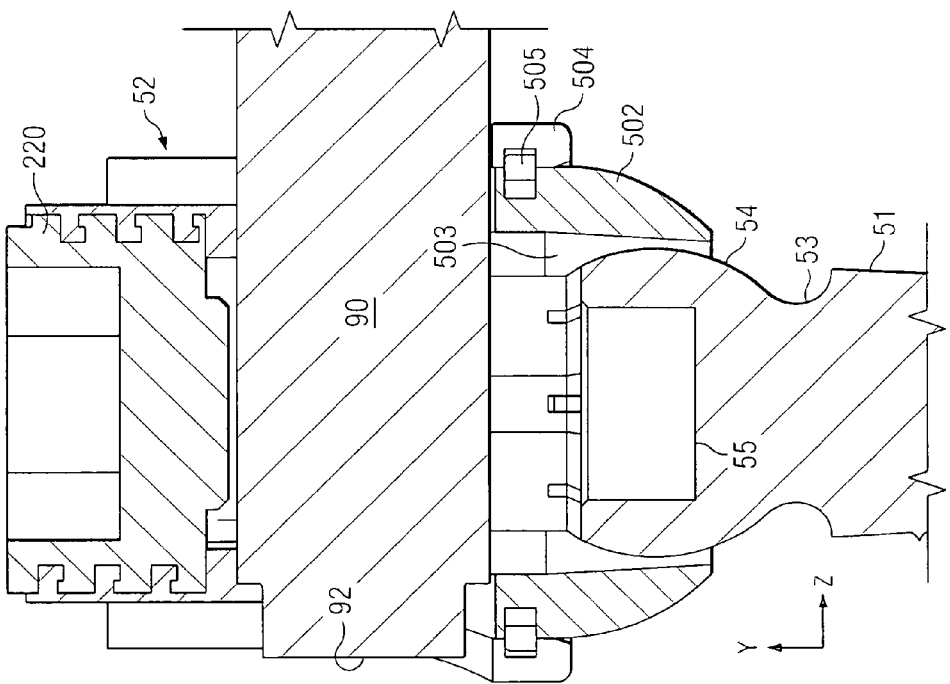

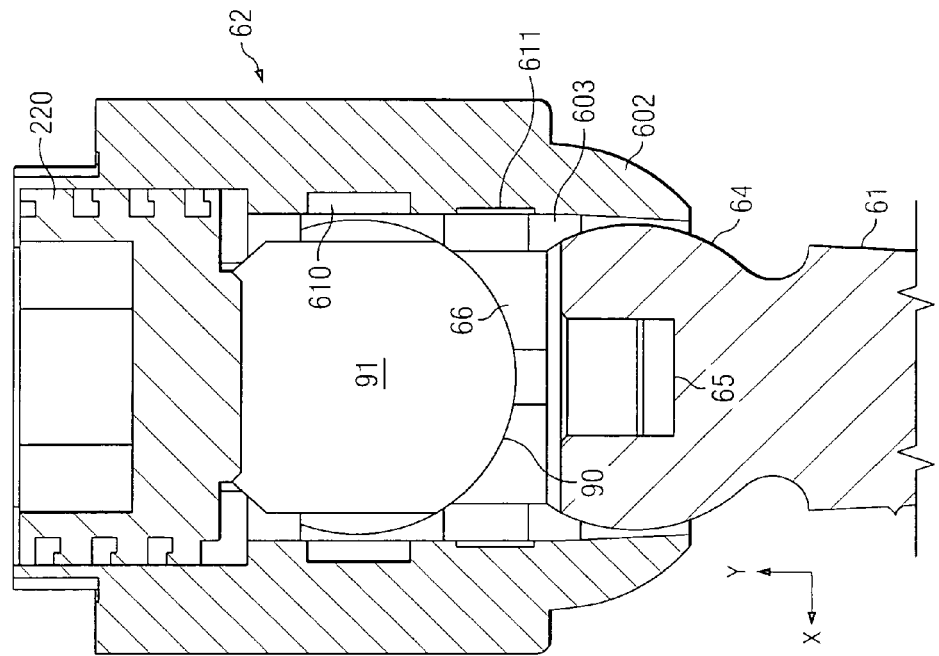
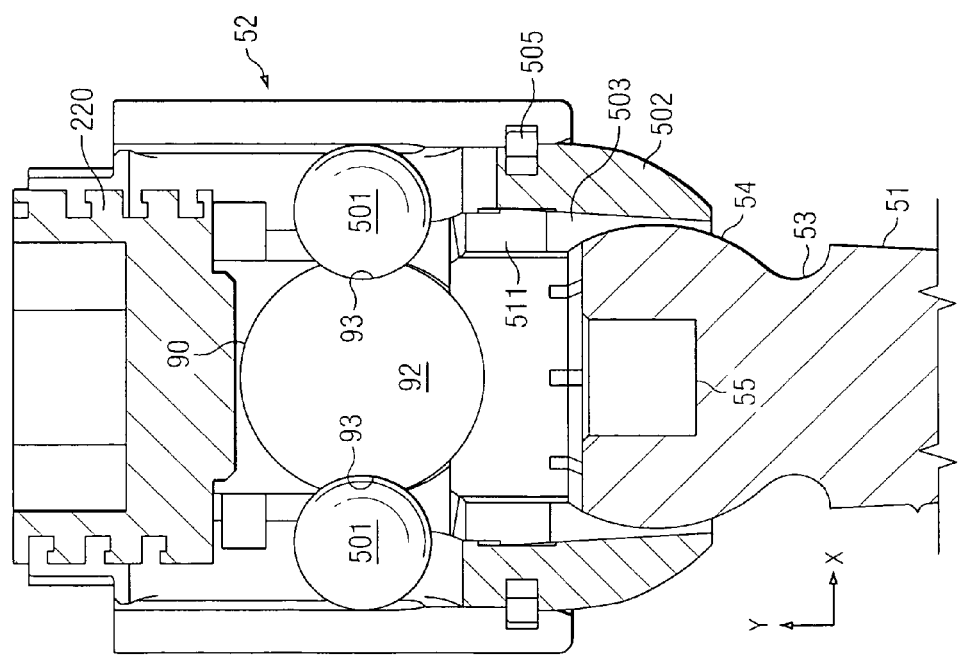

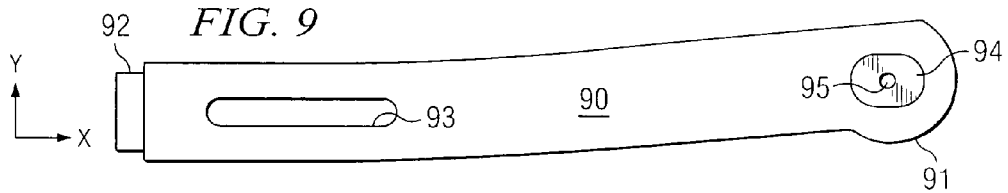
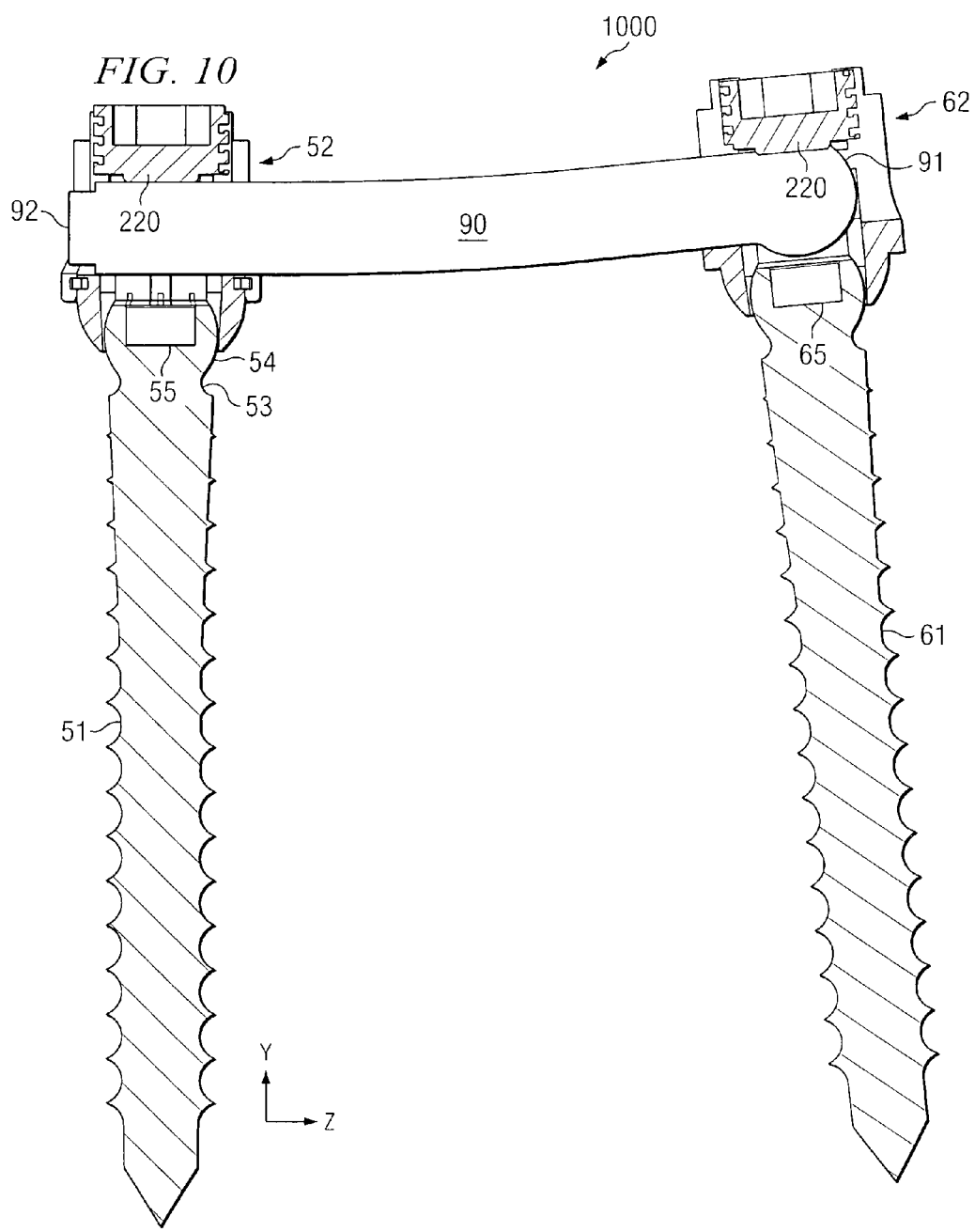

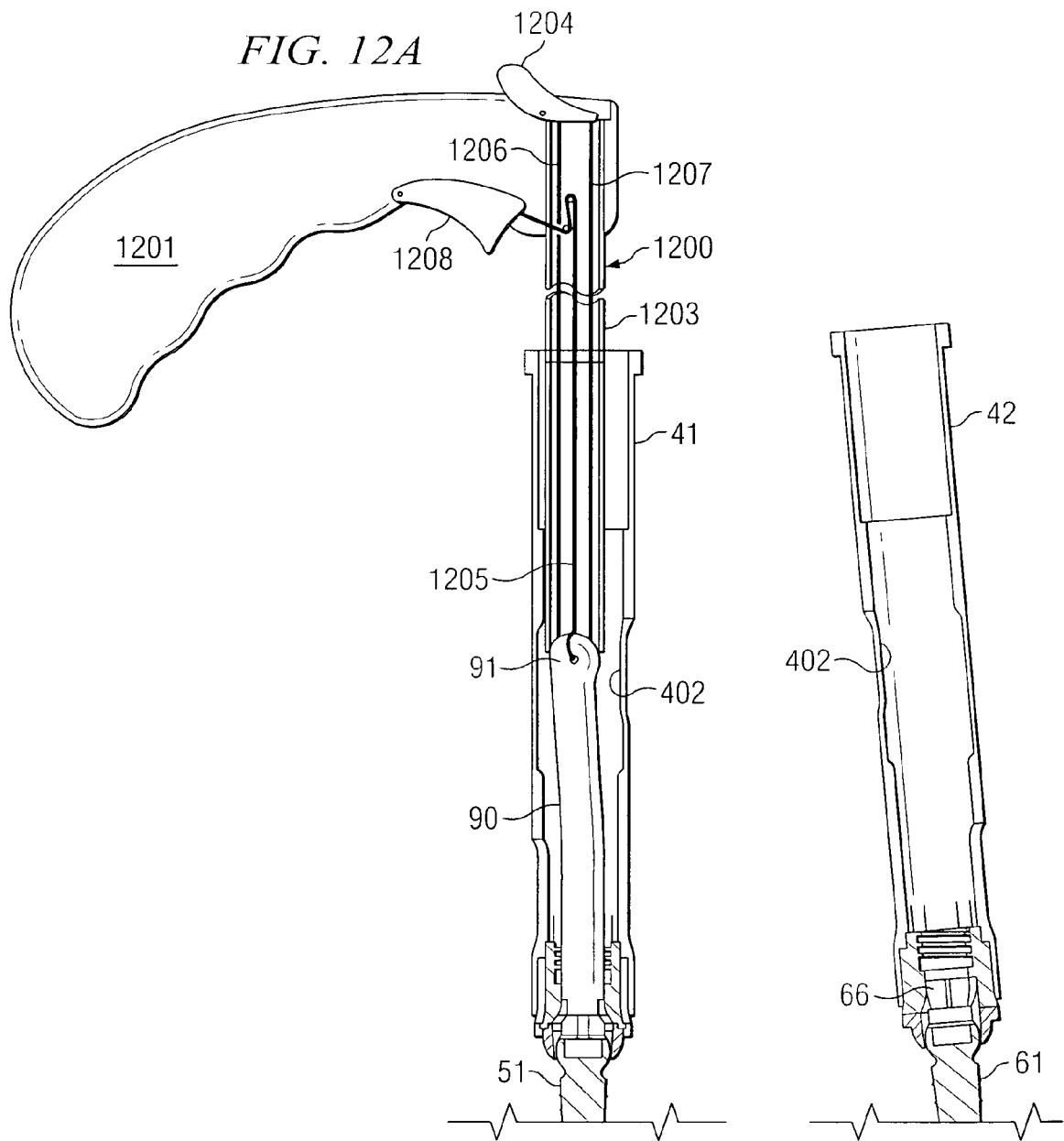

SYSTEM AND METHOD FOR STABILIZING OF INTERNAL STRUCTURES

TECHNICAL FIELD

This invention relates to bony structure stabilization systems and more particularly to systems and methods for percutaneously inserting a pedicle screw stabilization device.

BACKGROUND OF THE INVENTION

The human spine provides a vast array of functions, many of which are mechanical in nature. The spine is constructed to allow nerves from the brain to pass to various portions of the middle and lower body. These nerves, typically called the spinal cord, are located in a region within the spine called the neuro canal. Various nerve bundles emerge from the spine at different locations along the lateral length of the spine. In a healthy spine, these nerves are protected from damage and/or undue pressure thereon, by the structure of the spine itself.

The spine has a complex curvature made up of a plurality (24 in all) of individual vertebrae separated by intervertebral discs. These discs hold the vertebrae together in a flexible manner so as to allow a relative movement between the vertebrae from front to back and from side to side. This movement then allows the body to bend forward and back and to twist from side to side. Throughout this movement, when the spine is operating properly the nerves are maintained clear of the hard structure of the spine and the body remains pain free.

Over time, or because of accidents, the intervertebral discs loose height, become cracked, dehydrated, or are simply jarred out of position. The result being that the disc space height is reduced leading to compression of the nerve bundles causing pain and in some cases damage to the nerves.

Currently, there are many systems and methods at the disposal of a physician for reducing, or eliminating, the pain by minimizing the stress on the nerve bundles. In some instances, the existing disk is removed and an artificial disk is substituted therefore. In other instances, two or more vertebrae are fused together to prevent relative movement between the fused discs.

Often there is required a system and method for maintaining proper space for the nerve bundles that emerge from the spine at a certain location. In some cases a cage or bone graft is placed in the disc space to preserve height and to cause fusion of the vertebral level. As an aid in stabilizing the vertebrae, one or more rods or braces are placed between the fused vertebrae with the purpose of the braces being to support the vertebrae, usually along the posterior of the spine while fusion takes place. These braces are often held in place by anchors which are fitted into the pedicle region of the vertebrae. One type of anchor is a pedicle screw, and such screws come in a variety of lengths, diameters, and thread types.

One problem when connecting the braces to the anchors is to position the braces in place as quickly as possible and without doing more damage to the surrounding tissue and muscle of the patient as is absolutely necessary. For that reason, procedures have been developed that allow the physician to secure the anchors in the bony portion of the spine and to then connect the brace between the anchors. Techniques have been developed to allow the surgeon to perform this procedure in a minimally invasive manner, utilizing a percutaneous method.

In one such procedure, a first pedicle screw is inserted in a first vertebra to be stabilized. This screw is inserted using a tube, or cannula, extending through the patient's skin to the pedicle portion of the vertebrae. A second pedicle screw is inserted through a second cannula into the second vertebrae to be stabilized. Under current practice, the physician then must work the brace, or other supporting device, so that each brace end is positioned properly with respect to the preplaced pedicle screws. In order to properly position the brace ends fluoroscope pictures are taken as the brace is worked into position. It is difficult for the physician to know the exact orientation of the brace and even to know for certain when the brace ends have been properly positioned. U.S. Pat. No. 6,530,929 shows one instrument for positioning a stabilization brace between two preplaced anchors.

Another problem with both of the approaches discussed above, is that the braces must be made significantly longer than the distance between the pedicle screws to allow for proper attachment of the brace ends to the screws. Placement of the brace is sensitive to anchor alignment since the adjustment establishes the trajectory of the brace. If this trajectory is not established properly, the brace would have to pass through tissue, and, or bone that should not be touched. Also, the brace must enter a separate incision in the back of the patient. In addition to these, the learning curve for manipulation the insertion device of the '929 patent is greater than what should be required.

Another, more recent, approach has been to insert the cannulas over the respective pedicle areas of the vertebrae to be stabilized and then measure the distance between the cannulas. This measurement is then used to select, or cut, a rod, adding a bit to the dimension to ensure that the rod can be rigidly affixed to each anchor. In addition, each rod must be bent a certain amount (or a pre-bent rod utilized) to reflect the curvature of the spine. Once the proper rod dimension and shape is obtained each end of the rod is positioned in a separate one of the cannulas and the rod is worked downward toward the anchors passing through a separation of muscle and tissue from the skin line to the pedicle site. This placement of the rod is facilitated by a long handheld gripper which must then be manipulated to position the rod ends over the respective anchors so as to be captured by set screws in the tops of the respective anchors. Proper positioning of the rod ends is difficult, and requires repeated use of fluoroscopy to insure that the rod is fully seated and in a correct position.

BRIEF SUMMARY OF THE INVENTION

In one embodiment, there is shown a system and method for reducing the difficulty in percutaneous placement of a spine stabilization brace by coupling the brace to a pedicle screw in a single assembly. The brace-screw assembly is delivered along with an anchor extension through a cannula for anchoring in the vertebrae pedicle. The anchor extension, which becomes a cannula for working on the brace from the exterior of the patient, is constructed with partial slot openings along two sides. Once the screw portion of the brace-screw assembly is locked in place with respect to the first vertebra, the proximal end of the brace is below the skin line. The brace is then repositioned so that the proximal end leaves the cannula through one slot and is captured by a corresponding slot positioned in a second cannula coupled to a second anchor. Once captured, the proximal end of the brace is guided by the second cannula to a receptacle positioned in the second vertebrae. In one embodiment, the distal end of the brace is designed to adjust about the head of the first anchor and is further designed to allow for polyaxial as well as lateral movement, thereby adjusting for relative distances and angles between vertebrae.

The foregoing has outlined rather broadly the features and technical advantages of the present invention in order that the detailed description of the invention that follows may be better understood. Additional features and advantages of the invention will be described hereinafter which form the subject of the Claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended Claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 7A shows the brace-anchor assembly of FIG. 5A with the brace in a brace-down (rotated) position;

FIG. 7B is a cross-section view taken through line 7B-7B of FIG. 7A;

FIG. 7C is a cross-section view taken through line 7C-7C of FIG. 7A;

FIG. 8A shows the receiving cannula of FIG. 6A having captured a brace from an adjacent cannula;

FIG. 8B is a cross-section view taken through line 8B-8B of FIG. 8A;

FIG. 8C is a cross-section view taken through line 8C-8C of FIG. 8A;

FIG. 9 shows an embodiment of a hinged brace;

FIG. 10 shows an embodiment of a pair of anchors each firmly attached to a brace;

FIGS. 12A and 12B illustrate one embodiment of a tool for positioning the brace.

DETAILED DESCRIPTION

Figure 1:
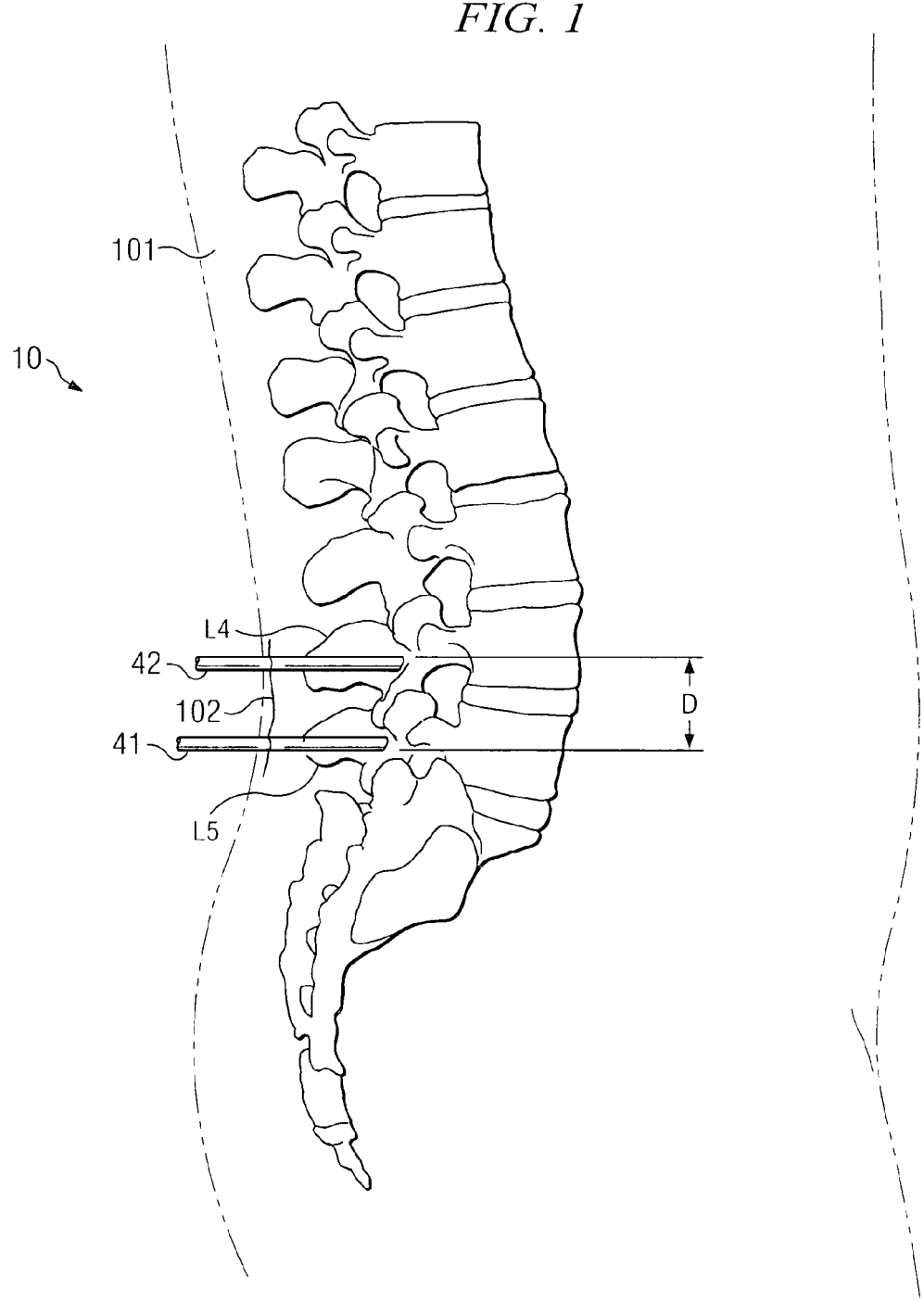
FIG. 1 is a sketch of the human spine showing a pair of cannulas positioned with respect to two vertebrae.

Turning now to FIG. 1, there is shown a sketch of human spine 10 showing a pair of tubes, or cannulas 41 and 42 extending through skin 101 into vertebrae L5 and L4. Cannula 41 is positioned over the pedicle of vertebrae L5 (as will be discussed), and cannula 42 is positioned over the pedicle of vertebrae L4. This procedure is being illustrated with respect to vertebrae L4 and L5 but could be performed with respect to any vertebrae or with respect to any bony portions of the body (human or animal) where a brace is to be placed between two points. The distance D is variable as desired. The sketch of FIG. 1, as are the sketches shown in other figures, are not to scale and are shown for illustration purposes with angles selected for clarity of explanation and not necessarily selected to be anatomically correct.

Figure 2A:
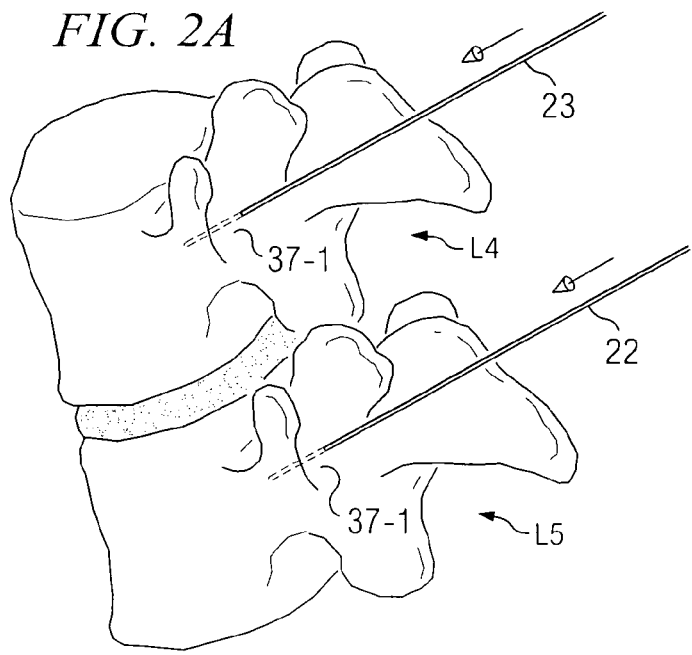
FIGS. 2A-2F show a cut-away view showing different stages of the installation of the stabilization device.
Figure 2B:
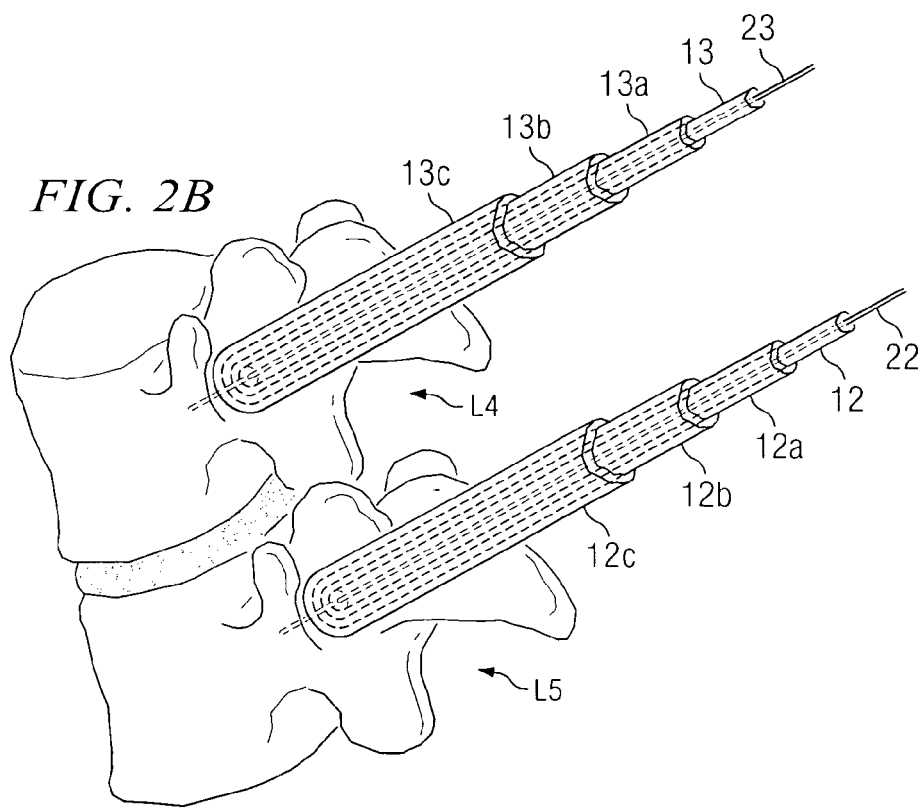

The procedure to insert the brace between vertebrae L5 and L4 is as follows: The surgeon identifies the desired vertebral levels and pedicle positions via standard techniques. Once the target vertebrae are identified, a small incision 102 is made through skin 101 and a tracking needle (or other device) is inserted to pinpoint exactly where each anchor is to be placed. A fluoroscope, or other x-ray technique, is used to properly position the tracking needle. Once the proper position is located, guide wire (K wire) 22 (FIG. 2A) is positioned with its distal end against the pedicle, in this case pedicle 37-1 of vertebrae L5. A guide wire 23 may be similarly positioned with its distal end against pedicle 37-1 of vertebrae L4, as shown in FIG. 2A. The surgeon then slides a series of continuing larger sized dilators 12, 12a, 12b, 12c down wire 22, and slides a series of continuing larger sized dilators 13, 13a, 13b, 13c down wire 23 as shown in FIG. 2B.

Approximately four or five dilators are used until a diameter suitable for passing the pedicle screw and its extensions is achieved. A tap is sent down over the K wire to tap a hole into the pedicle in preparation for receiving the anchor, which in this case is a pedicle screw. This tap will usually be a size slightly smaller than the pedicle screw thread size selected for that patient and that level.

Figure 2C:
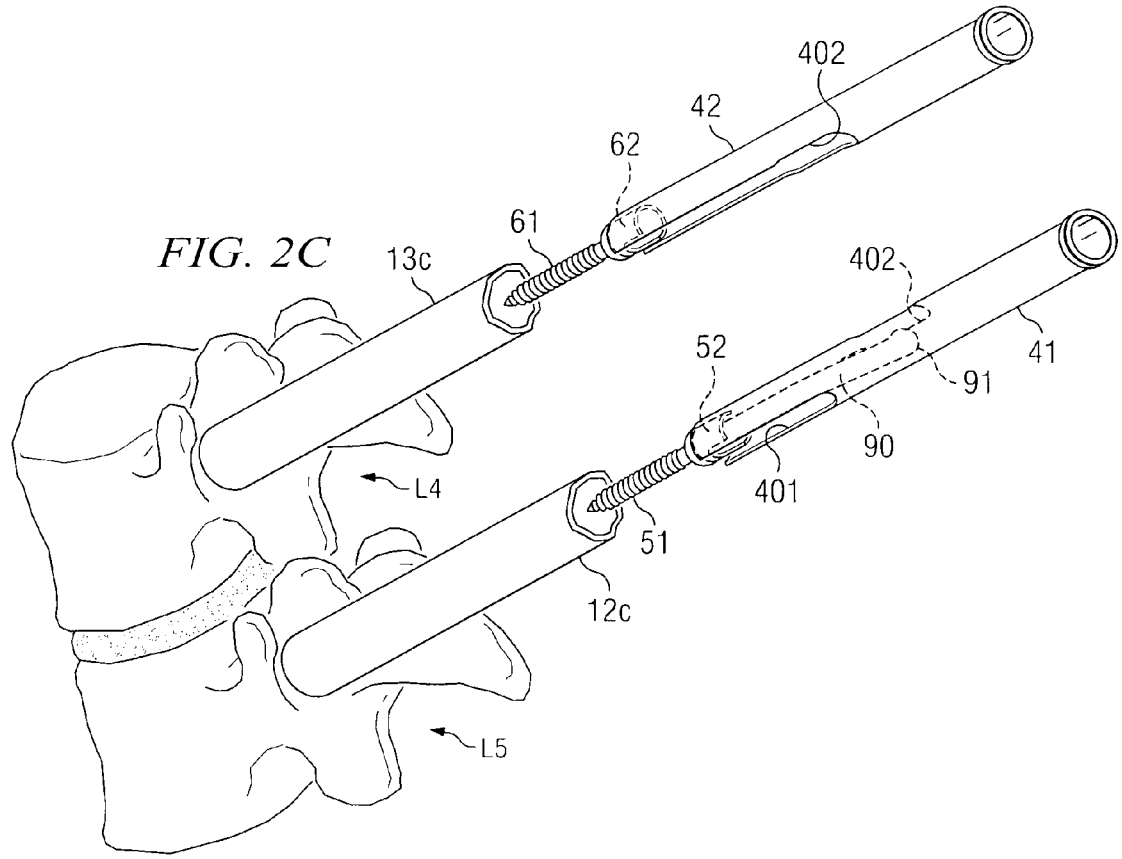
Figure 11:
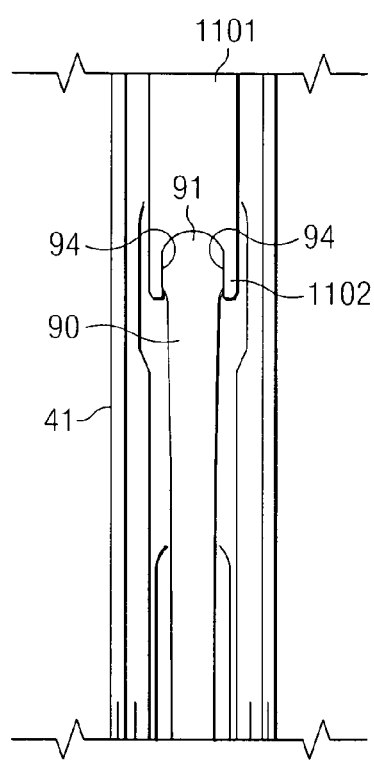
FIG. 11 illustrates one embodiment of a screw driver applying force to a brace.

After the hole is tapped and the K wire and the inner dilators, such as dilators 13, 13a, 13b, are removed, the surgeon is ready to introduce the anchor into the vertebrae. As shown in FIG. 2C, prior to inserting the anchor, brace 90 is attached to screw 51 to form a brace-screw assembly. This assembly is then positioned at the distal end of cannula 41 and a screwdriver or wrench (1101 shown in FIG. 11) is inserted into cannula 41 and attached to the proximal end 91 of brace 90. The entire assembly is then inserted into dilator 13C. The screwdriver engages with proximal end 91 of brace 90 so as to allow the surgeon to screw pedicle screw 51 into the pre-tapped hole in vertebrae L5. Pressure on the screwdriver forces the screw to be in-line with the brace, which, in turn, is in-line with the screwdriver. The screwdriver can be removeably attached to end 91 of brace 90 by engaging, for example, flat 94 (shown in FIG. 11) and/or hole 95 (shown in FIG. 9).

This same procedure would be repeated for each additional level, in this case level L4, except that screw 61 has assembly 62 affixed thereto. Assembly 62 is adapted to receive proximal end 91 of brace 90 as will be more fully described herein.

For a single level the above procedure is typically performed first on one side of both vertebral levels and then on the other side. When finished, four pedicle screws are inserted, holding two braces positioned laterally with respect to the center of the spine.

Once both screws are in place in vertebrae L5 and L4, dilators 12C and 13C are removed and, the surgeon slides a blunt dissection tool into incision 102 (FIG. 1) and gently parts the muscle bundle below the skin between vertebrae L4 and L5. Alternatively, the blunt dissection tool could go down the second cannula and, starting at the bottom of the second cannula 41, work open the muscle bundle between the cannula working upward as far as is necessary. Using this procedure, the muscles (and other tissue), only need be separated to a point where the brace 90 must pass. Thus, the separation need not go to the skin level. This reduces trauma even further.

Figure 2D:
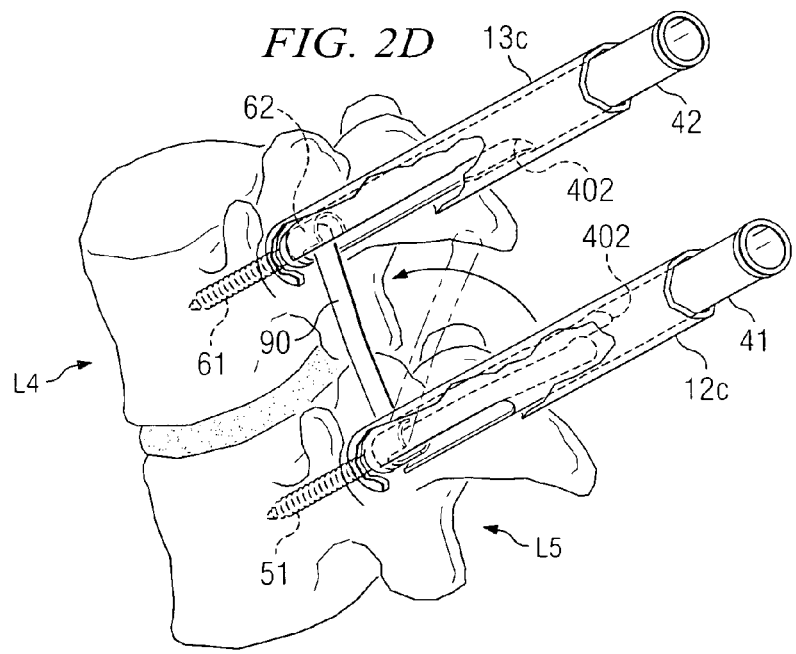
Figure 12B:
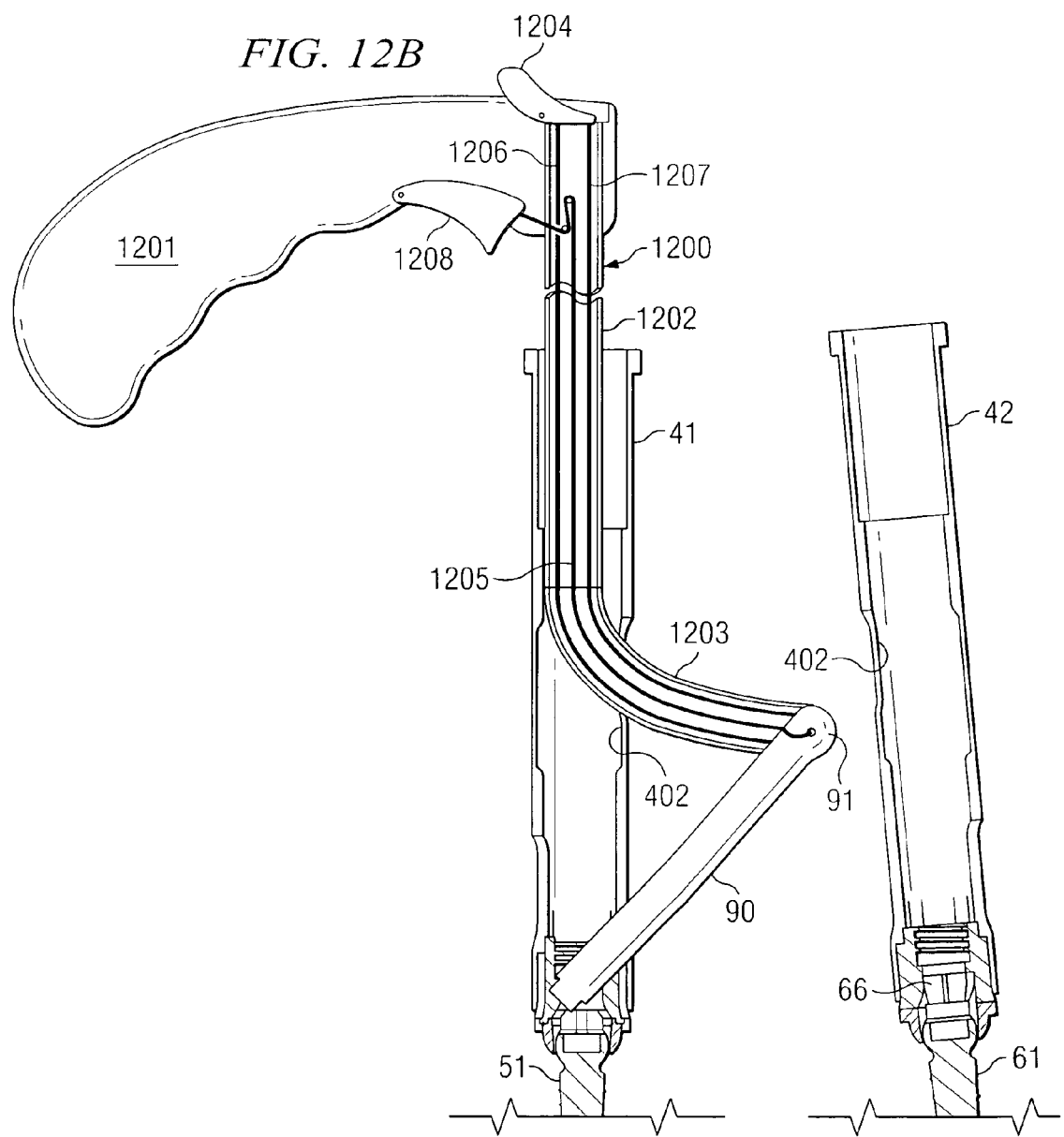

Once an opening in the muscles has been developed between cannulas 41 and 42, brace 90 is then positioned, by pivoting, as shown in FIG. 2D, by sliding a tool (for example, tool 1200, FIG. 12A) down cannula 41 to engage proximal end 91 of brace 90. The tool could have a force fit with end 91 or as shown in FIG. 12A, can have handle 1201 and trigger control 1204 for controlling removable attachment with brace 90. One or more wires 1205, 1206 and 1207 extending inside tool portions 1202, 1203, can be controlled by triggers 1204 and 1208 so that spring loaded grips (not shown) controlled by wire 1202 can mate with hole 95 (shown in FIG. 9). Trigger 1208 can control wire 1205 to releasably grip end 91 of brace 90. Once portion 1203 is mated with end 91 of brace 90 the surgeon can pull the tool slightly outward to disengage brace end 92 from screw 51. The surgeon can then operate wires 1206 and 1207, via trigger 1204, or otherwise, which wires pull on one side of tool portion 1203 to bend tool portion 1203, as shown in FIG. 12B. This bending forces brace end 91 out of cannula 41 (through opening 402 thereof) and through the prepared muscle opening and into opening 402 of cannula 42. Once within cannula 42, tool end 1203, under control of the surgeon, manipulates brace end 91 down cannula 42 and into a mating relationship with screw 61. Once this mating relationship is achieved, (as will be discussed) tool end 1203 is released from brace end 91, under control of wire 1205 and tool 1200 is removed from both cannulas. Wires 1206 and 1207 are used on opposite sides of tool 1200 under control of trigger 1208 to control bending and unbending of tool portion 1203. Note that only temporary locking mechanism and/or tool bending mechanism, including pneumatic and hydraulic can be used, if desired.

Slots 402 of the respective cannulas are positioned fully under the skin line 101 of the patient. Brace 90 can have any shape desired. It can be flat, oval or rod shaped and the cross-section need not be constant in shape or diameter.

The surgeon receives positive feedback (a sensory event), either by feel (for example, a snap action) or by sound (for example, a click), or both when brace 90 is properly mated with assembly 62. If desired, one or both of assembly 52 or 62 mounted to the respective pedicle screws 51 and 61 can be angularity adjusted (as will be discussed) to accommodate the patient's body structure. The polyaxial nature of assemblies 52 and 62 with respect to the anchors allows for such adjustments which are necessary for a variety of reasons, one of which is that the angulation between adjacent vertebral pedicles varies.

Figure 2E:
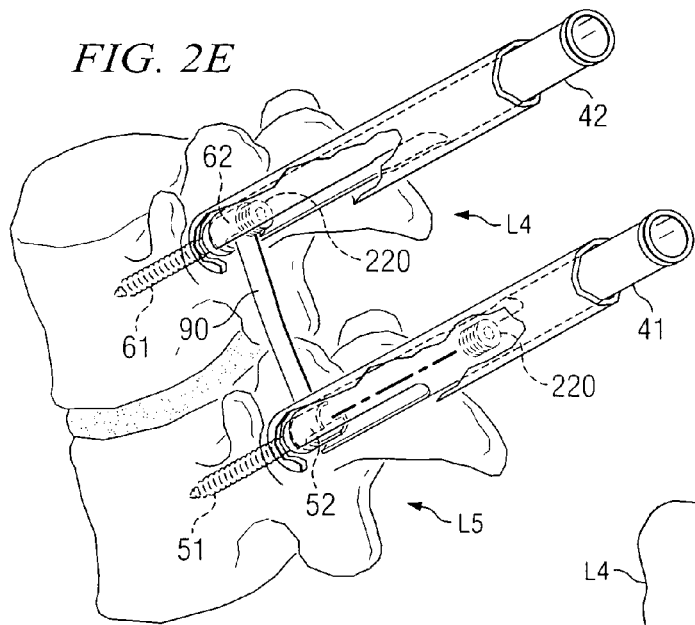

As shown in FIG. 2E, after all angular and lateral adjustments are made, set scres 220, or other locking devices, are introduced down cannulas 41 and 42 to lock each end of brace 90 to its respective pedicle screw.

Figure 2F:
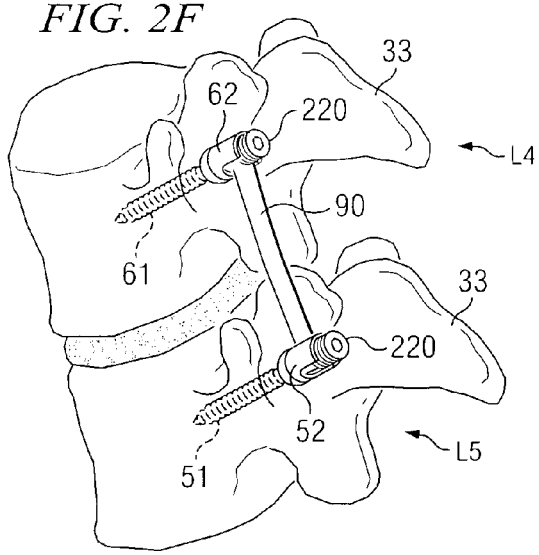

As shown in FIG. 2F, once the proximal end of brace 90 is snapped in place to screw 61 and set screws 220 are tightened, cannulas 41 and 42 can be removed and the incision closed. As discussed, this procedure would then be repeated on the opposite side of spinous process 33.

Figure 3A:
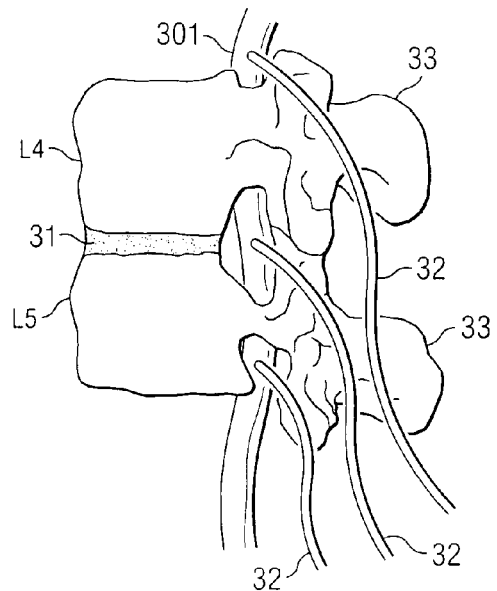
FIG. 3A shows a side view of two vertebrae.

FIG. 3A is a lateral view of two vertebrae segments and L5 and L4. Nerve roots 32 are shown coming out from spinal cord 301. The nerve roots become compressed when vertebrae L4 collapses down upon vertebrae L5 when disc 31 becomes reduced in size due to injury, a dehydration or otherwise. Spinous processes 33 form a portion of the posterior of the vertebral bodies.

Figure 3B:
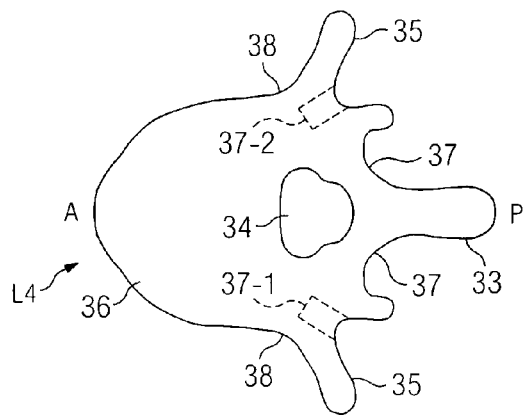
FIG. 3B shows a top view of a single vertebrae.

FIG. 3B is a top view of vertebrae L4 and is similar to other lumbar levels. A Vertebra L4 includes vertebral body 36, spinous process 33, neuro canal 34, and transverse processes 35. The pedicle region, such as pedicle 37, is the bony area bridged roughly between outer wall 38 and neuro frame 34. Areas 37-1 and 37-2 are the target areas for the pedicle screws, as discussed above.

Figure 4:
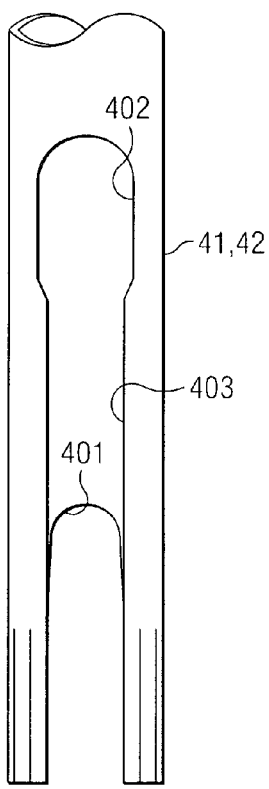
FIG. 4 shows an embodiment of a slated cannula.

FIG. 4 shows cannulas 41 and 42 which could be identical, if desired. Cannula 41 includes opening 401 to allow for lateral adjustment of the distal end of brace 90. On cannula 42, opening 402 can be adjusted downward from that of cannula 41 (because of the arc of brace 90) so as to more precisely capture and retain proximal end 91 of brace 90. Also, as will be seen, the opening 402 on cannula 42 can be adopted to receive the shape of end 91 of brace 90, and lower opening 401 eliminated, if desired.

Figure 5A:
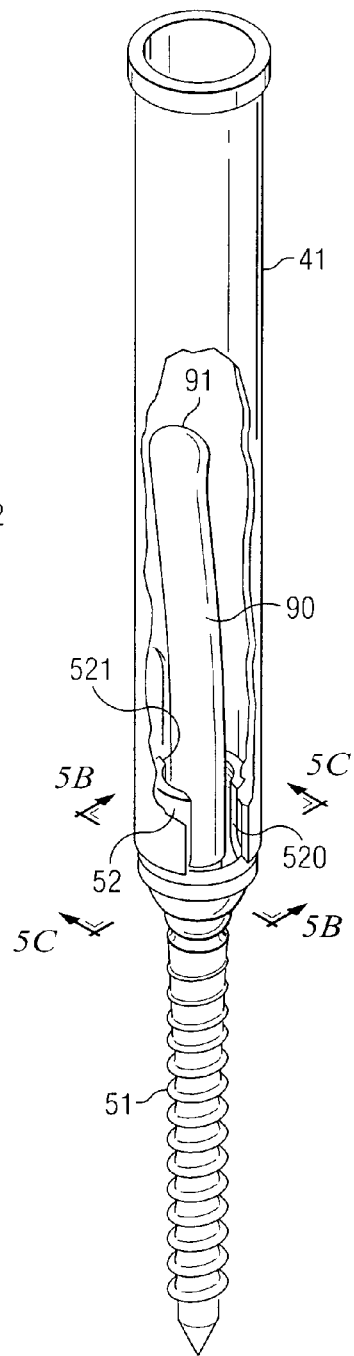
FIG. 5A shows a brace-anchor assembly within a cannula.

FIG. 5A shows pedicle screw 51, and brace rod adjustment assembly 52. Assembly 52 acts as a hinge for brace 90 positioned within cannula 41. Screw portion 51 is extended out from the base of the connection in an in-line orientation with brace 90. By the application of torque to proximal end 91 of brace 90 by a screwdriver (or wrench), as discussed above, and or as shown in FIG. 11, screw 51 can be turned so that it can be screwed into the bone as desired. Note that assembly 52 has two openings 520 and 521 which, as will be seen, allow brace 90 to pivot.

Figure 6A:
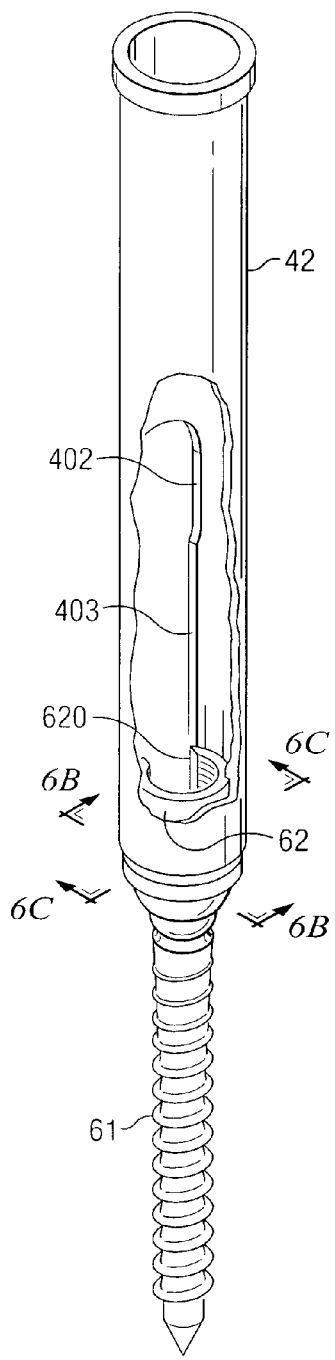
FIG. 6A shows the receiving cannula attached to a receiving anchor.

Screw 51 is connected to assembly 52 as will be described herein. This combination is attached to the distal end of cannula (extension) 41 by, for example, constructing flexible fingers at the distal end of cannula 41 and constructing on the inside of these fingers protrusions in the form, for example, of small pyramids. These pyramids then fit into a tight mating relationship with mating structures constructed on the parity of assembly 52. When it is desired to release cannula 41 from assembly 52, upward pressure and perhaps a tap is applied to the ring at the proximal end of cannula 41. That upward force causes the fingers to fly outward. Thereby releasing the above-described mated structures. This same arrangement is used to assemble and release cannula 42 from assembly 62 (FIG. 6A)

Figure 5B:
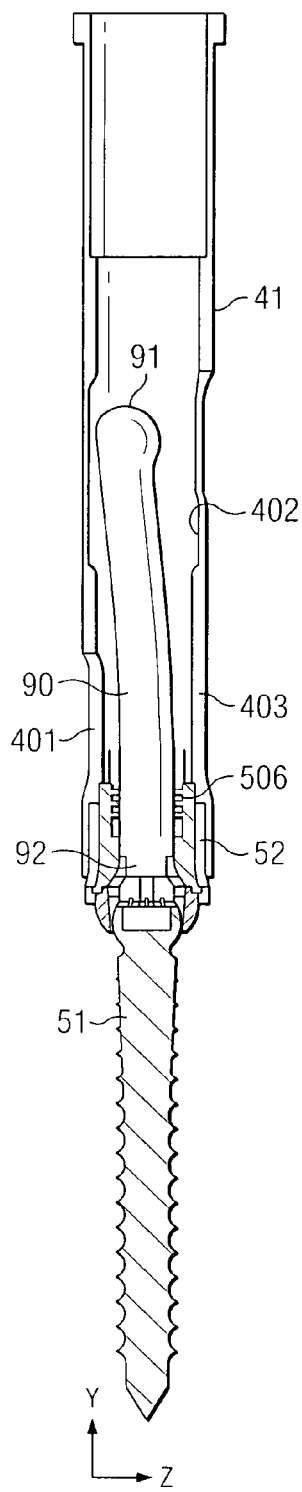
FIG. 5B is a cross-section view taken through line 5B-5B of FIG. 5A.

FIG. 5B is a cross-section taken through line 5B-5B of FIG. 5A and shows screw 51 attached to brace 90 via assembly 52. Brace 90 is shown curved to approximate the spinal curvature. The length of brace 90 is selected to show the distance between the respective anchors. For the L5-L4 level this distance is approximately 35 mm to 45 mm.

Figure 5C:
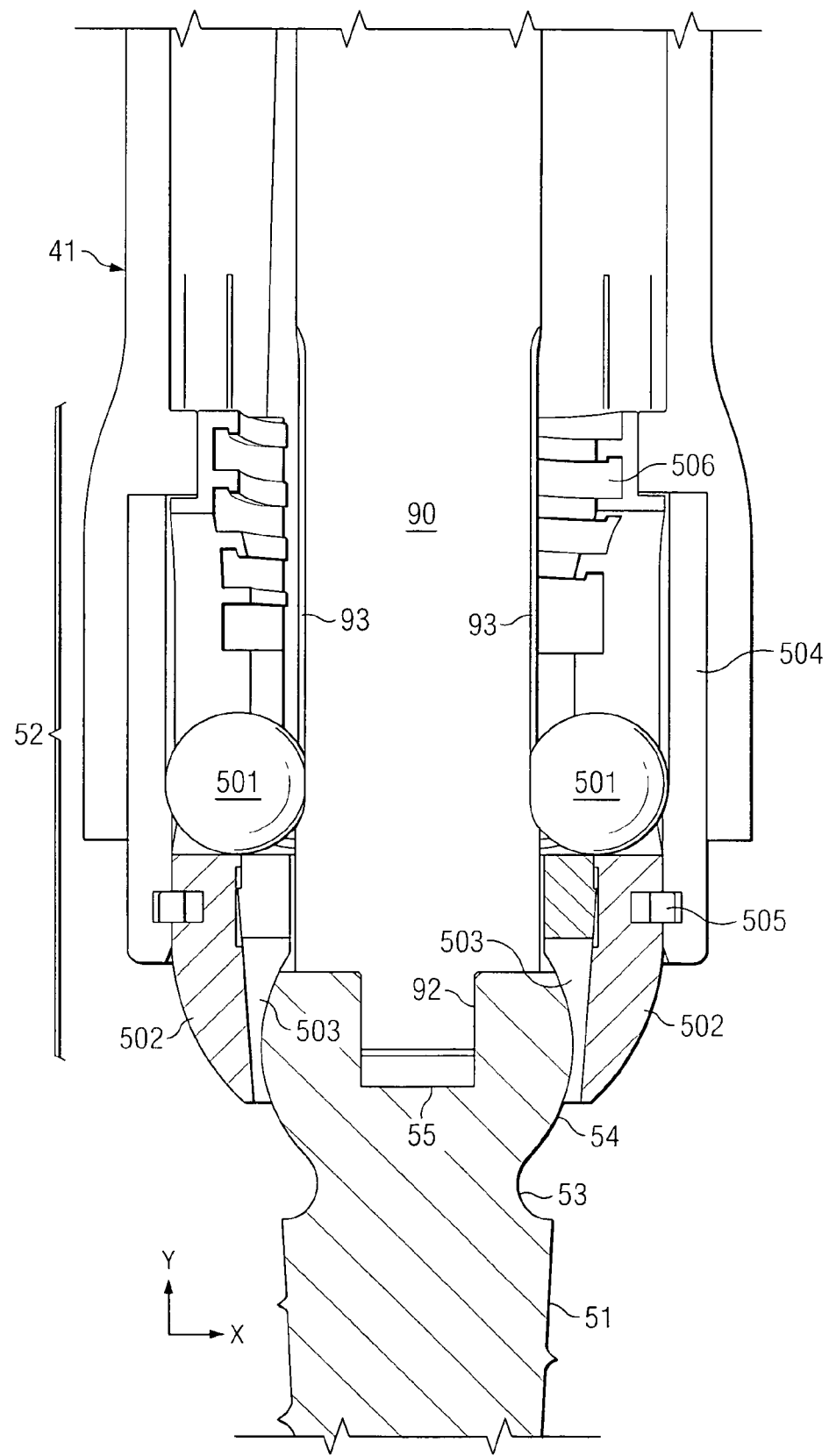
FIG. 5C is a cross-section view taken through line 5C-5C of FIG. 5A.

FIG. 5C shows screw 51 having neck 53 and head 54. Screw 51 also has recess area 55 designed for mating with end 92 of brace 90. This mating call be a slot or other flat configuration or any means of connecting two structures together so that force (in this embodiment the force is torque) can be delivered from one to another. Brace 90 will, when desired, lift upward so as to unmate end 92 from flat 55 so that brace 90 can then pivot with respect to assembly 52. Bearings 501 positioned in slots 93 of brace 90 facilitate such pivoting. Slots 93 serve to limit the in-line and lateral distance brace 90 can move. Bearings 501 also serve as a pivot point for brace 90 and to prevent brace 90 from turning.

Assembly 52 allows brace 90 to move from the in-line position to a rotated position while also accommodating the lateral motion of brace 90. This lateral motion accommodates different lateral distances between anchors. Assembly 52 can be constructed in different ways and from different materials as desired, for example, as shown in U.S. Pat. No. 5,672,176 hereby incorporated by reference herein. When brace 90 is repositioned to approximately a 90° angle and a set screw (not shown) is in place within threads 506, pressure is applied downward on the side of brace 90. This action, in turn, applies pressure on clamp 502, forcing wedge 503 against head 54 of screw 51. This then locks the polyaxial mechanism in place and prevents brace 90 from further movement with respect to screw 51. This clamping action also maintains the relative angular position between brace 90 and screw 51. Spring band 505 snaps between a groove in clamp 502 and a groove in shell 504 holding assembly 52 together. Note that assembly 52 can be separate from screw 51 as shown or can be constructed integral thereto. Also note that the polyaxial motion described is not necessary and can be eliminated, if desired.

FIG. 6A shows cannula 42 having slot 403, with opening 402 positioned to receive end 91 of brace 90. Once end 91 is captured within slot 402, end 91 passes down inside cannula 42 crrying brace 90 down slot 403 toward assembly 62. Slot 620 in assembly 62 allows brace 90 to enter assembly 62.

Figure 6B:
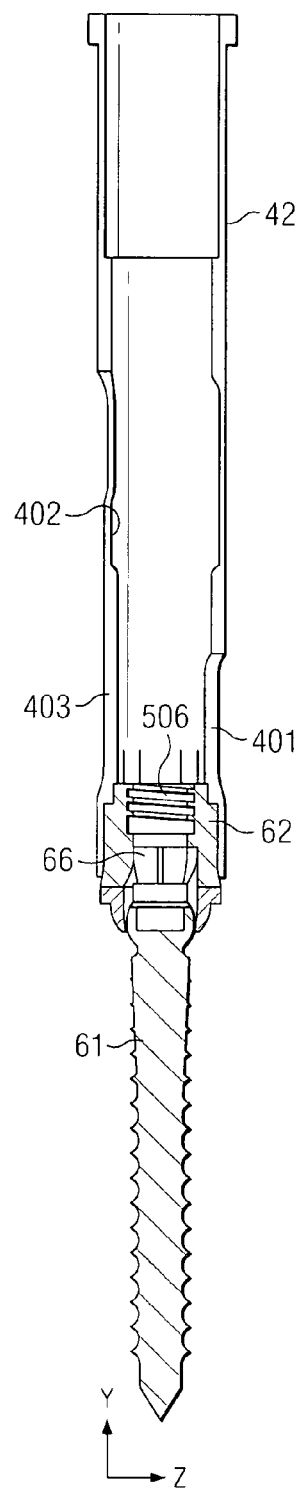
FIG. 6B is a cross-section view taken through line 6B-6B of FIG. 6A.

FIG. 6B is a cross-section taken along lines 6B-6B of FIG. 6A, and shows assembly 62 with receptacle 66. Receptacle 66 is designed, in one embodiment, to snap together with end of brace 90. This snap-action provides positive feed back to the surgeon, either by feel or audibly, or both. This tactile (or audible) feed back is caused, for example by end 91 passing into receptacle 66. In one embodiment, a force fit could be achieved between end 91 and receptacle by making the inner circumference of the outer rim of receptacle 66 smaller than the diameter of end 91. Mating can be facilitated by cutting small grooves or slots in receptacle 66 to allow receptacle 66 to expand around end 91 for a locking fit. This expansion occurs as end 91 enters into receptacle 66. As the mating occurs, end 92 of brace 90 (FIG. 7A) is free to move laterally with respect to anchor 51 since brace 90 is held in place (as discussed above) by bearings 501 riding in slots 93 (FIG. 7C).

Figure 6C:
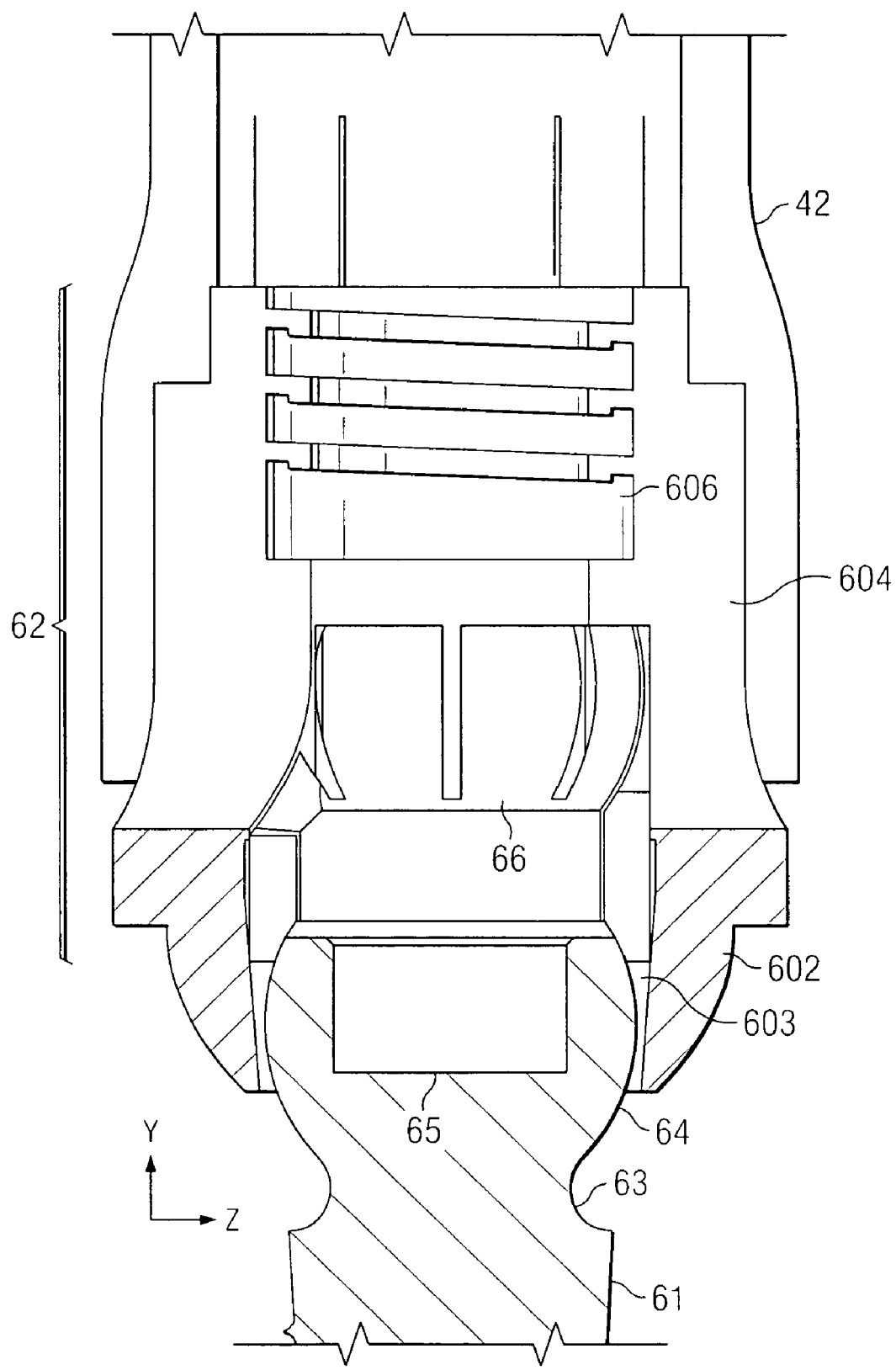
FIG. 6C is a cross-section view taken through line 6C-6C of FIG. 6A.

FIG. 6C shows an expanded view of assembly 62 mounted to head 64 of screw 61. Receptacle 65 accepts a wrench or screw driver from the surgeon for inserting screw 61 into the bone and is accessible through the base of receptacle 66. Clamp 602 acts on wedge 603 to apply force on head 64 of screw 61. Until tightened fully by a set screw positioned within threads 505, assembly 62 is free to rotate polyaxially around head 64 of anchor 61. This polyaxial movement can, if desired, be eliminated.

FIG. 7A shows the brace/screw assembly with brace 90 repositioned approximately 90° with respect to screw 51. Screw 51 would be embedded in a bony structure (or other hard structure), not shown in FIG. 7A. In a particular application, the exact rotation will depend upon many factors, including the angle between anchors and the angle the respective anchors make with respect to the bone in which they are imbedded.

FIG. 7B slows a cross-section taken along line 7B-7B of FIG. 7A. As shown, brace 90 is rotated approximately 90° with respect to assembly 52. End 92 of brace 90 has been disengaged from mating structure 55 on head 54 of screw 51. In FIG. 7B, set screw 220 is shown about to press down on brace 90 to compress brace 90 to screw head 54, as previously discussed.

FIG. 7C is a cross-section taken through line 7C-7C of FIG. 7A and again shows brace 90 rotated 90° with respect to screw 51. Lateral movement of brace 90 (in and out of the page in FIG. 7C and left and right in FIG. 7B) is facilitated by berings 501 riding in grooves 93 of brace 90 and acting both as a fulcrum and as lateral limitation. All such movement is inhibited when set screw 220 presses down on brace 90. Wing 511 on clamp 503 prevents clamp 503 from upward movement.

FIG. 8A shows the receptacle/screw assembly with brace 90 positioned in its capture mode with respect to assembly 62. Assembly 62 is, in turn, mounted on head 64 of screw 61. Screw 61 would be embedded in a second bony structure (on other hard structure) not shown in FIG. 8A.

FIG. 8B shows a cross-section taken along line 8B-8B of FIG. 8A. End 91 of brace 90 is captured by receptacle 66. Set screw 220 is shown applying downward pressure on brace 90 in order to lock brace 90 to screw head 64 as previously discussed. The inner geometry of receptacle 66 is keyed to match the proximal end of brace 90.

FIG. 8C shows a cross-section taken along line 8C-8C of FIG 8A. End 91 of brace is shown mated with receptacle 66 and locked tight by set screw 220. Once set screw 220 presses down on brace 90, hinge assembly 62 clamps against head 64 of screw 61 to prevent further movement of brace 90 with respect to screw 61. Area 610 is created in assembly 62 such that receptacle 66 can expand as brace end 91 passes into the receptacle. Wing 611 on wedge 603 prevents wedge 603 from moving upward.

FIG. 9 shows one embodiment of brace 90 with distal end 92 and proximal end 91. Slot 93 is longer than actually necessary to allow for lateral movement of brace 90 during the seating process so as to allow for different distances between anchors. As discussed, distal end 92 can have any shape required for mating with head 54 of screw 51 for the purpose of force transfer. Also note that proximal end 91 has a ball (or partial ball) shape for capture by slot 402 of cannula 42. End 91 can have any shape, provided such shape is adapted for capture by cannula 42.

FIG. 10 shows a single level brace system 1000 having brace 90 with its distal end 92 clamped tightly with respect to screw 51 (a first anchor) and its proximal end 91 clamped tightly with respect to screw 61 (a second anchor). Each of these anchors is firmly supported in a respective bony structure (not shown in FIG. 10) of a patient. Note that brace 90 is slightly curved to, at least partially, adjust for the spine curvature. Also note that the respective anchors are not necessarily parallel to each other but each has assumed an angle necessary for proper placement in the pedicle (or other bony area) of the respective vertebra. While the brace has been shown with respect to the L4 and L5 vertebrae, the system, method, and device discussed herein are not so limited and can be used between any bony or other hard portions that must be supported, including single level or multilevel.

For bracing two or more levels, one option is to skip one or more vertebral levels onto the anchor, another option is to use a "pass-through" anchor assembly on the skipped vertebral level(s). The pass-through assembly can be adapted for locking to the brace on the portion of the brace passing through the middle assemblies. Another option would be to have a dual headed anchor on the center vertebra which accepts braces, one brace from each of the other surrounding levels.

Although the present invention and its advantages have been described in detail, it should be understood that various changes, substitutions and alterations can be made herein without departing from the invention as defined by the appended Claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended Claims are intended to include within their scope such processes, machines, manufacture, compositions of matter, means, methods, or steps.

What is claimed is:

1. A medical implant system comprising:
a first bone anchor having a first proximal head and a first distal threaded shank;
a second bone anchor having a second proximal head and a second distal threaded shank; and
a brace assembly comprising:
a shell coupled to the first proximal head;
a brace having a longitudinal axis and a slot longitudinally displaced along the brace;
a pair of bearings displaced on opposite sides of the brace and positioned between the brace and the shell, each of the pair of bearings riding within the slot longitudinally displaced along the brace, wherein the bearings allow for slidingly adjusting and pivoting the brace relative to the first proximal head along at least a portion of a longitudinal length of the brace;
wherein the brace assembly farther comprises means for transmitting torque between the brace and the first distal threaded shank that includes a first key at a distal end of the brace temporarily mated to a recess area on the first proximal head.

2. A medical implant system comprising:
a first bone anchor having a first proximal head and a first distal threaded shank;
a second bone anchor having a second proximal head and a second distal threaded shank; and
a brace assembly comprising:
a shell coupled to the first proximal head;
a brace having a longitudinal axis and a slot longitudinally displaced along the brace;
a pair of bearings displaced on opposite sides of the brace and positioned between the brace and the shell, each of the pair of bearings riding within the slot longitudinally displaced along the brace, wherein the bearings allow for slidingly adjusting and pivoting the brace relative to the first proximal head along at least a portion of a longitudinal length of the brace; and
wherein the brace has a first position in which a longitudinal axis of the brace is generally in line with a longitudinal axis the first bone anchor and a second position in which the longitudinal axis of the brace is pivoted approximately 90 degrees from the first position.

3. A medical implant comprising:
a first bone anchor having a first proximal head and a first distal threaded shank; and
a brace assembly coupled to the first proximal head, the brace assembly comprising:
a brace having a first end portion and a second end portion; and
a pair of bearings displaced on opposite sides of the brace, each of the pair of bearings riding within a slot longitudinally displaced along the brace, wherein the brace has a first position in which a longitudinal axis of the brace is generally in line with a longitudinal axis of the first bone anchor and a second position in which the longitudinal axis of the brace is pivoted approximately 90 degrees from the first position.

4. The medical implant of claim 3 wherein the first proximal head is polyaxially coupled to the brace assembly.

5. The medical implant of claim 3 wherein the first end portion of the brace is at least partially ball shaped.

6. The medical implant of claim 3 wherein the brace is curved.

* * * * *

UNITED STATES PATENT AND TRADEMARK OFFICE
CERTIFICATE OF CORRECTION

PATENT NO. : 7,588,588 B2  Page 1 of 1
APPLICATION NO. : 10/690211
DATED : September 15, 2009
INVENTOR(S) : Spitler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 708 days.

Signed and Sealed this

Twenty-first Day of September, 2010

David J. Kappos
*Director of the United States Patent and Trademark Office*